United States Patent [19]

Yamasaki et al.

[11] 4,300,014

[45] Nov. 10, 1981

[54] PROCESS FOR ISOMERIZATION OF XYLENE

[75] Inventors: Yasuo Yamasaki; Tokuji Sakai; Tamio Onodera; Kiji Sumitani, all of Matsuyama, Japan

[73] Assignee: Teijin Petrochemical Industries Ltd., Tokyo, Japan

[21] Appl. No.: 204,018

[22] Filed: Nov. 4, 1980

[30] Foreign Application Priority Data

Aug. 4, 1980 [JP] Japan .................................. 55-106380

[51] Int. Cl.$^3$ .................................................. C07C 5/24
[52] U.S. Cl. ....................................... 585/481; 252/419
[58] Field of Search ........................... 585/481; 252/419

[56] References Cited

U.S. PATENT DOCUMENTS

| | | | |
|---|---|---|---|
| 3,986,982 | 10/1976 | Crowson et al. | 252/419 |
| 4,007,131 | 2/1977 | Gillespie et al. | 252/419 |
| 4,152,363 | 5/1979 | Tabak et al. | 252/419 X |
| 4,163,028 | 7/1979 | Tabak et al. | 585/481 |
| 4,176,084 | 11/1979 | Luckenbach | 252/419 |

*Primary Examiner*—John F. Niebling
*Attorney, Agent, or Firm*—Sherman & Shalloway

[57] ABSTRACT

A process for isomerizing xylenes, which comprises contacting an aromatic hydrocarbon feedstock containing mainly a xylene isomeric mixture containing ethylbenzene with a catalyst of a palladium-containing crystalline aluminosilicate in the vapor phase in the presence of hydrogen to continuously isomerize xylenes and simultaneously de-ethylate the ethylbenzene selectively;

interrupting the isomerization reaction;

introducing an oxygen-containing gas into a bed of the catalyst in which coke has been deposited during the isomerization reaction, to contact the catalyst with the oxygen-containing gas;

burning off the coke deposits on the catalyst with the oxygen-containing gas by gradually increasing the temperature of introduction of the oxygen-containing gas from not more than 200° C. to a temperature in the range of 330° to 390° C. with no part of the catalyst bed exceeding a maximum temperature of 400° C. while controlling the hot spot temperature of the catalyst bed not to exceed 50° C. throughout the burn-off period;

reducing in hydrogen the catalyst from which the burnable coke deposits have been removed at least partly;

and thereafter resuming the isomerization reaction in the presence of the regenerated catalyst.

20 Claims, 2 Drawing Figures

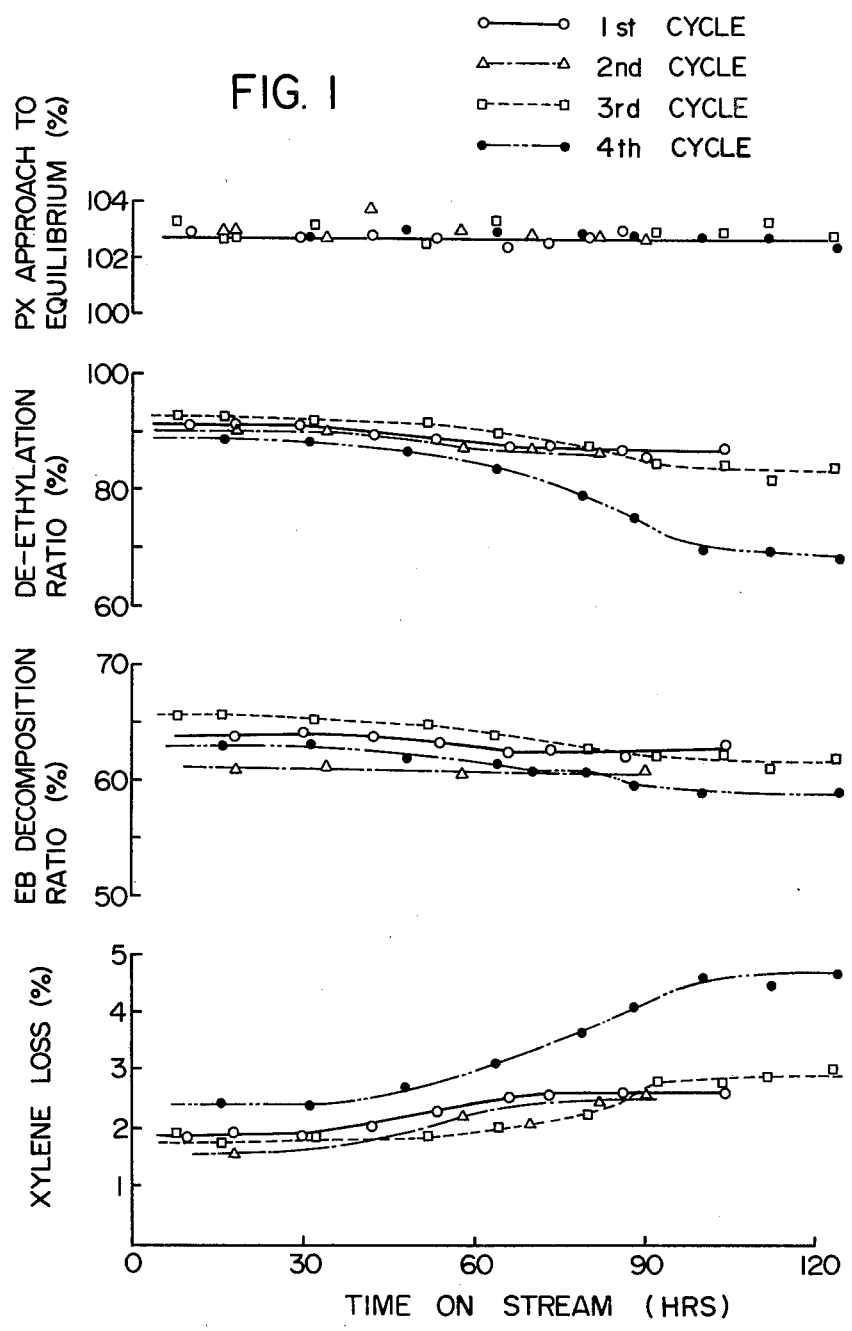

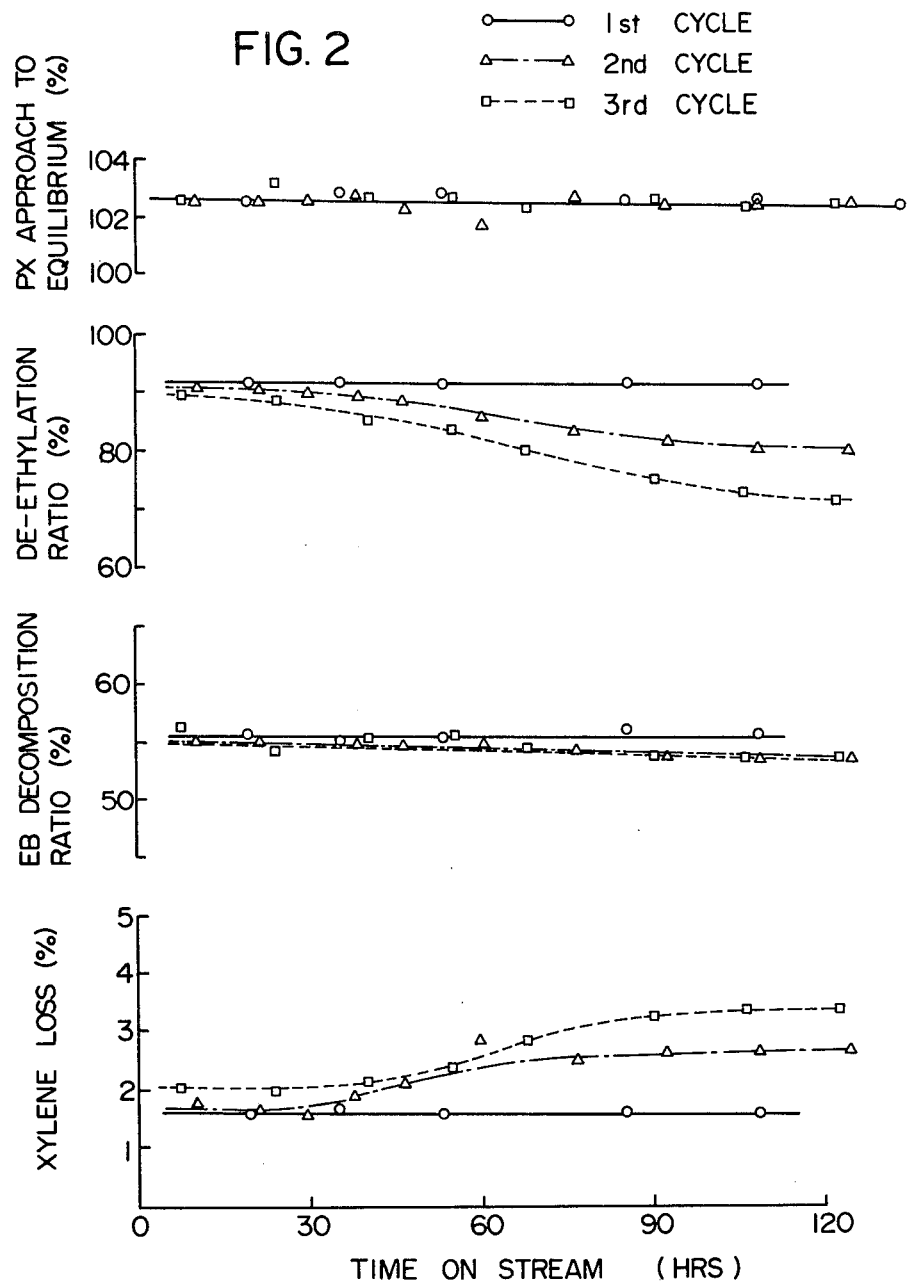

PROCESS FOR ISOMERIZATION OF XYLENE

This invention relates to a process for isomererization of xylenes. Particularly, it relates to a process for isomerization of xylenes which comprises contacting a xylene isomeric mixture containing ethylbenzene with a palladium-containing crystalline aluminosilicate catalyst in the vapor phase in the presence of hydrogen to isomerize xylenes continuously and simultaneously to de-ethylate the ethylbenzene selectively, characterized in that the catalyst is effectively regenerated and re-used.

Many catalysts have been proposed heretofore for the conversion of hydrocarbons. A typical example is a dual functional catalyst composed of a solid acid and a noble metal of Group VIII of the periodic table having a hydrogenating and dehydrogenating ability, which is frequently used in the rearrangement reaction of various hydrocarbons using hydrogen.

A catalyst composed of a noble metal of Group VIII of the periodic table (e.g., nickel, platinum) and a crystalline aluminosilicate has already been known for the isomerization of xylenes including de-ethylation of ethylbenzene, and this catalyst has excellent activity. For example, U.S. Pat. No. 4,152,363 discloses a process which comprises isomerizing xylenes at a temperature of 800° F. to 1,000° F. using a catalyst containing 0.1 to 5% by weight of crystalline aluminosilicate zeolite having a silica/alumina ratio of at least 12, and the specification of this U.S. patent states that the crystalline aluminosilicate zeolite may contain an element of Group VIII of the periodic table such as nickel, platinum, iron, cobalt or palladium.

U.S. Pat. No. 4,163,028 discloses a process which comprises isomerizing xylenes at a temperature of at least 800° F. using a zeolite catalyst having a silica/alumina ratio of at least 500. The specification of this U.S. patent states that the zeolite may preferably contain a metallic ion, particularly a platinum ion.

The processes described in these U.S. patents are characterized by the fact that it is suitable for the isomerization of xylenes containing ethylbenzene, and simultaneously with the isomerization reaction of xylenes, ethylbenzene is dealkylated to benzene and ethane as main products.

These U.S. patents recommend the use of catalysts composed of ZSM-series zeolites (particularly ZSM-5) and metals of Groups VIII of the periodic table, specifically ZSM-series zeolite catalysts containing platinum.

The isomerization reactions of xylenes using these ZSM-series zeolite catalysts containing platinum are carried out at a relatively high temperature of about 800° F. or more at a relatively high weight hourly space velocity ("WHSV" for short). This is because at lower temperatures, the ability of the zeolite catalyst containing platinum to hydrogenate the benzene ring becomes very high, and the xylenes are converted to naphthenes resulting in an increased loss of the xylenes. Since this tendency becomes more pronounced as the WHSV decreases, the xylenes cannot be isomerized at a high p-xylene approach to equilibrium with a low loss of xylenes unless the isomerization reaction is carried out at a high temperature of at least about 800° F. and at a certain high WHSV. Thus, when a zeolite catalyst containing platinum is used, the reaction must be carried out under severe conditions involving high temperatures and high WHSV values. Consequently, this causes the industrial disadvantage that the activity of the catalyst is reduced early, and the number of catalyst regenerating operations within a given period increases. Moreover, since the zeolite catalyst containing platinum has de-methylating activity, the use of this catalyst for the isomerization of xylenes causes a large loss of xylenes owing to de-methylation.

On the other hand, when a zeolite containing palladium is used as an isomerization catalyst, the p-xylene approach to equilibrium and the ethylbenzene decomposition ratio are nearly the same as those attained by the use of a zeolite containing platinum even under mild conditions involving relatively low temperatures and low WHSV values. But the zeolite containing palladium has a much lower ability to hydrogenate the benzene ring, and a loss of xylenes owing to the formation of naphthenes and demethylation is small. Another advantage is that since it exhibits high isomerizing activity even at low temperatures and low WHSV, a reduction in its activity is little even when it is used for a long period of time.

Thus, the zeolite containing palladium is suitable as a catalyst for the isomerization of xylenes containing ethylbenzene.

However, when conventional catalyst regenerating methods intended mainly for the regeneration of platinum-containing zeolites are applied to the regeneration of palladium-containing zeolites, the activity of the catalyst is reduced as a result of the regeneration.

In particular, the ability of the catalyst to deethylate ethylbenzene is extremely reduced. This is a serious defect which precludes industrial utilization of zeolites containing palladium in spite of the aforesaid superior adavantages.

For example, U.S. Pat. No. 3,986,982 discloses a process for regenerating a catalyst consisting essentially of an acid-resistant alkali-metal deficient mordenite containing a platinum group metal hydrogenating component within its pores, which has become deactivated during the selective hydrocracking of n-paraffins in a waxy hydrocarbon feedstock, said process comprising burning off the catalyst with a stream of inert gas and oxygen at a temperature controlled to a maximum of 550° C., the water content of the gas at the inlet being below 200 ppm by volume, thereafter subjecting the catalyst to chlorine treatment at 400° to 550° C., purging the catalyst to remove residual oxygen and chlorine, and then reducing the catalyst. The U.S. patent mentions palladium as well as platinum as the platinum group metal, but the working examples in the specification cover only the use of platinum. When this process is used in the isomerization reaction of xylenes using a palladium-containing zeolite catalyst, the activity of the regenerated catalyst is reduced because of the low water content of the regenerating gas and the high regenerating temperature.

It is an object of this invention to provide, in a process for isomerizing xylenes which comprises contacting an aromatic hydrocarbon feedstock containing mainly a xylene isomeric mixture containing ethylbenzene with a bed of a palladium-containing crystalline aluminosilicate-based catalyst in the vapor phase in the presence of hydrogen to continuously isomerize the xylenes and simultaneously to deethylate the ethylbenzene selectively, the regeneration of the catalyst of which activity has been reduced as a result of the reaction to an activity close to its initial activity.

Another object of this invention is to provide an industrial process for achieving the isomerization of a xylene isomeric mixture in the presence of the aforesaid catalyst which simultaneously involves selective deethylation of ethylbenzene, said process including a step of activating the palladium-containing crystalline aluminosilicate-based catalyst.

Other objects and advantages of this invention will become apparent from the following detailed description.

According to this invention, there is provided a process for isomerizing xylenes, which comprises contacting an aromatic hydrocarbon feedstock containing mainly a xylene isomeric mixture containing ethylbenzene with a palladium-containing crystalline aluminosilicate catalyst in the vapor phase in the presence of hydrogen to continuously isomerize xylenes and simultaneously de-ethylate the ethylbenzene selectively;

interrupting the isomerization reaction;

introducing an oxygen-containing gas into a bed of the catalyst in which coke has been deposited during the isomerization reaction, to contact the catalyst with the oxygen-containing gas;

burning off the coke deposits on the catalyst with the oxygen-containing gas by gradually increasing the temperature of introduction of the oxygen-containing gas from not more than 200° C. to a temperature in the range of 330° to 390° C. with no part of the catalyst bed exceeding a maximum temperature of 400° C. while controlling the hot spot temperature of the catalyst bed not to exceed 50° C. throughout the burn-off period;

reducing in hydrogen the catalyst from which the burnable coke deposits have been removed at least partly;

and thereafter resuming the isomerization reaction in the presence of the regenerated catalyst.

According to the process of this invention, xylenes can be isomerized by using a palladium-containing crystalline aluminosilicate-based catalyst having a high p-xylene approach to equilibrium and a high ethylbenzene decomposition ratio (de-ethylation ratio) with a small loss of the xylenes. When the catalyst whose activity has been reduced as a result of long-term use is regenerated by the process of this invention, its activity is restored substantially to the initial activity, and the catalyst can be used again in the isomerization of xylenes as a highly active isomerization catalyst having the great ability with isomerization and de-ethylation. Furthermore, similar effects can be obtained even when this regenerating treatment is repeated.

The aromatic hydrocarbon feedstock used in the isomerization of xylenes in this invention predominantly contains xylene isomers which have not attained a thermodynamic equilibrium composition. As is well known, xylene has three isomers, ortho-, meta- and para-isomers. It is known that when a mixture in an arbitrary ratio of the three isomers is subjected to an isomerization reaction, the reaction reaches an equilibrium when the ratio among the three isomers reaches a certain specific value, and apparently no further advance of the isomerization is noted. The composition of the xylene isomers in such an equilibrium state is called the "thermodynamic equilibrium composition". The thermodynamic equilibrium composition varies slightly depending upon temperature, and for example, the xylene isomers have the following thermodynamic equilibrium compositions at the following temperature.

[I] Mixture consisting only of three xylene isomers (at 327° C.)

| p-Xylene | 23.8% by weight |
| m-Xylene | 53.3% by weight |
| o-Xylene | 22.9% by weight |

[II] Mixture of xylene isomers and ethylbenzene (at 327° C.)

| Ethylbenzene | 6.0% by weight |
| p-Xylene | 22.4% by weight |
| m-Xylene | 50.1% by weight |
| o-Xylene | 21.5% by weight |
| | (100% by weight in total) |

In the present specification, the term "xylene isomeric mixture not attaining a thermodynamic equilibrium composition" denotes xylene isomers in which the concentration of at least one of the three xylene isomers falls outside the thermodynamic equilibrium composition.

The aromatic hydrocarbon feedstock used as a starting material in the process of this invention necessarily contains ethylbenzene in addition to the xylene isomers. It may further contain another aromatic hydrocarbon such as benzene, toluene, ethyltoluene, trimethylbenzene, diethylbenzene, ethylxylene and tetramethylbenzene. It is desirable in this case that the amount of the xylene isomeric mixture present be generally at least 30% by weight, preferably at least 50% by weight, based on the weight of the aromatic hydrocarbons feedstock.

$C_8$ aromatic hydrocarbon fractions obtained by reforming, thermal cracking or hydrocracking of naphtha can be used especially advantageously as the aromatic hydrocarbon feedstock in the process of this invention. These fractions contain ethylbenzene of the same number of carbons in addition to the xylene isomers. Very good results can be obtained in the process of this invention when using a $C_8$-aromatic hydrocarbon fraction which contains the xylene isomers and ethylbenzene in a total amount of at least 80%, preferably at least 90% by weight, based on the weight of the fraction.

Desirably, the aromatic hydrocarbon feedstock contains at most 40% by weight of ethylbenzene.

The palladium-containing crystalline alumino-silicate-based catalyst used in the isomerization of the aromatic hydrocarbon feedstock contains as an active catalytic ingredient a Pd-zeolite material in which palladium is held substantially in the metallic state on a crystalline aluminosilicate substrate.

The crystalline aluminosilicate (to be sometimes referred to as "zeolite") forming the base of the catalyst used in this invention contains mainly hydrogen or a hydrogen precursor such as an ammonium ion at a cation site and has a silica/alumina mole ratio of at least 10, preferably from 20 to 1,000, more preferably from 30 to 200. In other words, a so-called highsilica zeolite having a high silica content relative to alumina is used as a base of the catalyst. Many zeolites having a high silica content relative to alumina have been suggested heretofore, and a zeolite having an extremely high silica content represented by a silica/alumina mole ratio of as high as 2,000 is also known. In the present invention, there is conveniently used as a highsilica zeolite which has a relatively low silica/alumina ratio and therefore has a relatively high acid activity attributed to the alumina component.

In using a conventional high silica-containing zeolite catalyst, it was the practice to use it in combination with a basic substance such as an amine or to destroy a part of its acid site by treatment with steam and to shorten the contact time and increase the treating temperature (for example, to at least 800° F.) for the purpose of decreasing the acid activity of the catalyst and thus promoting the hydrodealkylation of alkylbenzenes, particularly mono-alkylbenzenes, and inhibiting side-reactions such as disproportionation, transalkylation, etc. (see U.S. Pat. No. 4,101,595). In the present invention, zeolites having a relatively high degree of acid activity can be directly used without subjecting them to such a treatment.

Any known high-silica zeolites can be used in this invention if their silica/alumina mole ratio is within the above-specified range.

Typical examples of crystalline aluminosilicates or zeolites that can be used in this invention as a catalyst base include various ZSM series zeolites developed by Mobil Oil Corporation, and zeta-series zeolites developed by Imperial Chemical Industries, Ltd. The ZSH series zeolites are preferred.

Examples of ZSM-series zeolites are ZSM-5 (see U.S. Pat. No. 3,702,886), ZSM-11 (U.S. Pat. No. 3,709,979), ZSM-12 (see U.S. Pat. No. 3,832,449), ZSM-35 (see U.S. Pat. No. 4,016,245) and ZSM-38 (see U.S. Pat. No. 4,046,245) and ZSM-38 (see U.S. Pat. No. 4,046,859). Examples of zeta-series zeolites are zeta 1 (see German Offenlegungsschrift No. 2,548,697), and zeta 3 (see German Offenlegungsschrift No. 2,548,695).

TP-1 series zeolites discovered by the present inventors as high-silica zeolites (see Japanese Laid-Open Patent Publication No. 137,500/79) can also be used. These TP-1 series zeolites are obtained by heating a starting mixture containing silica, alumina, alkali metals and water at a temperature and for a time sufficient to form crystalline aluminosilicates by using organic sulfur compounds such as thiols, sulfides, sulfoxides, sulfones or thiophenes. The properties of these TP-1 series zeolites and their production are described in detail in the specification of the Japanese Laid-Open Patent Publication cited above.

These zeolites are generally available in a form containing an alkali metal ion or an alkaline earth metal ion at the cation site. In the present invention, these zeolites are converted to H-form zeolites, and used in the form containing mainly hydrogen or a hydrogen precursor at the cation site. Accordingly, unless otherwise specified, "zeolite", as used in the present application, denotes an H-form zeolite.

It has been found that the use of ZSM-5 zeolite as a catalyst base produces the best effect. Hence, according to the most preferred embodiment of this invention, ZSM-5 zeolite is used as a base of the isomerization catalyst.

In the process of this invention, the crystalline aluminosilicate (zeolite)-based catalyst containing palladium is used as an isomerization catalyst.

As stated hereinabove, a zeolite catalyst containing platinum has the excellent ability to isomerize xylenes, but simultaneously catalyzes hydrogenation of the benzene ring and demethylation of the xylenes. These catalytic activities cause undesirable side-reactions in the isomerization of xylenes and lead to a loss of the xylenes. However, when palladium is incorporated into the zeolite, it is possible to effectively inhibit its catalytic activity on the undesirable reactions such as the hydrogenation of the benzene ring and the de-methylation of the xylenes while maintaining a high xylene isomerizing ability equivalent to the platinum-containing zeolite.

In the present specification and the appended claims, the term "palladium-containing crystalline alumino-silicate (zeolite)" means that palladium is included in the zeolite in a condition in which palladium is ion-exchanged at the cation site of zeolite, and/or a condition in which palladium physically adheres to the surface of the zeolite.

The palladium-containing zeolite may be prepared by methods generally known in the modification of zeolites with metallic elements. To facilitate an understanding of these methods, typical examples of these are described in detail below.

In industrially useful zeolites, their cation site is generally substituted by an ion of an alkali metal such as potassium or sodium or an ion of an alkaline earth metal such as calcium, and therefore, a step is taken to exchange the alkali metal or alkaline earth metal ion with hydrogen or an ammonium ion. This exchange may be performed simultaneously with the modification of the zeolites with palladium metal, or prior to that time.

One typical method for performing the exchange comprises dipping a zeolite whose cation site has been substituted by an alkali metal or alkaline earth metal ion in an aqueous solution containing a palladium ion and an ammonium ion. By this method, there is obtained a modified zeolite in which at least a greater portion of the cation site is of an ammonium ion form and which is modified with palladium. When the resulting palladium-modified zeolite of an ammonium ion form is then calcined at a temperature of about 200° to 600° C. it can be converted to a hydrogen ion-form zeolite modified with palladium.

Another method involves treating a zeolite having its cation site substituted by an alkali metal or alkaline earth metal ion with an inorganic acid such as hydrochloric acid or sulfuric acid or an organic acid such as acetic acid or oxalic acid to convert a greater portion of the cation site to a hydrogen ion form, and ionically exchanging it with palladium or depositing palladium thereon.

Still another method involves treating a zeolite having its cation site substituted by an alkali metal or alkaline earth metal ion with an aqueous solution of a water-soluble ammonium compound to obtain a zeolite having a greater portion of its cation site substituted by an ammonium ion, and ionically exchanging the cation site with palladium or depositing palladium thereon either directly or after the zeolite has been calcined at a temperature of, say, 250° to 650° C. to convert it to an H-form zeolite. In this method, the treatment of substituting an ammonium ion can be easily performed by contacting the zeolite with a 5 to 20% by weight aqueous solution of a water-soluble ammonium compound such as ammonium chloride or ammonium nitrate.

Ion exchanging of zeolite with palladium and/or deposition of palladium on the zeolite can be carried out by methods known per se for exchanging a zeolite with a metal and/or depositing the metal thereon.

For example, the zeolite to be treated is contacted with an aqueous or nonaqueous medium having dissolved therein the desired palladium compound. Examples of such palladium compounds include the halides, oxides, sulfides, oxy acid salts and complex compounds of palladium. For example, palladium may be deposited on zeolite by impregnating the zeolite with an aqueous solution of a water-soluble palladium compound and then evaporting the water. Or palladium may be ionically exchanged by dipping zeolite in an aqueous solution of a palladium compound having an ion-exchange ability such as a palladium complex, filtering the dipped zeolite and sufficiently washing the zeolite.

If desired, before modification treatment of the zeolite with palladium, the zeolite may be calcined at a temperature of 100° to 700° C., preferably 200° to 600° C., in an oxygen atmosphere such as air or an inert gaseous atmosphere such as nitrogen for a period of 1 to 50 hours. Generally, a better catalyst can be obtained by performing this calcination.

The zeolite modified with palladium in this manner may preferably be calcined at a temperature of 100° to 700° C., preferably 200° to 600° C., in an oxygen-containing atmosphere such as air or in an inert gaseous atmosphere such as nitrogen for a period of about 1 to about 50 hours.

The resulting palladium-containing zeolite can be used in the isomerization reaction of xylenes in a finely divided form, or optionally after it is molded into the desired shapes such as pellets or tablets as in the usual practice. In molding the palladium-containing zeolite, the zeolite is mixed with a synthetic or natural refractory inorganic oxide, such as silica, alumina, silica-alumina, kaolin or silica-magnesia, which is usually used as a binder for zeolite-type catalysts, and the mixture is molded into the desired shape. The molded product is then calcined to a solidified product. Advatageously, the amount of the palladium-containing zeolite as an active catalyst ingredient in the molded product is generally 1 to 99% by weight, preferably 10 to 90% by weight, based on the weight of the molded product.

Prior to use, the palladium-containing zeolite catalyst is treated at a temperature of 200° to 600° C., preferably 250° to 550° C., in a reducing atmosphere such as hydrogen gas. Usually, this reduction treatment is performed after the catalyst has been filled into a reactor.

Advantageously, the amount of palladium included in the crystalline aluminosilicate is generally 0.01 to 2% by weight, preferably 0.02 to 1.5% by weight, more preferably 0.05 to 1% by weight, based on the weight of the crystalline alumino-silicate.

The catalyst of this invention so prepared, before reduction and use in the isomerization reaction, contains palladium usually in the form of a cation and/or an oxide. When it is reduced prior to the isomerization reaction, palladium is converted to an elemental form.

Isomerization of the aromatic hydrocarbon feedstock can be performed under known reaction conditions by using the above specified palladium-containing zeolite-based catalyst. The reaction temperature is generally 250° to 450° C., preferably 270° to 400° C., especially preferably 280° to 380° C., and the partial pressure of hydrogen is generally 0 to 25 kg/cm².G, preferably 0 to 20 kg/cm².G, especially preferably 0 to 12 kg/cm².G.

In the practice of the process of this invention, the starting aromatic hydrocarbon feedstock is fed at a rate which can be varied widely according to the type of the hydrocarbon feedstock used, the type of the catalyst, etc. It is generally advantageous to feed the hydrocarbon feedstock at a weight hourly space velocity (WHSV) of about 1 to about 500, preferably 2 to 100, more preferably 3 to 50, hr$^{-1}$.

In the present specification and the appended claims, the "weight hourly space velocity" is a value calculated in accordance with the following equation.

$$\frac{\text{Weight of the hydrocarbon feedstock fed per hour}}{\text{Weight of the catalyst}}$$

The "weight of the catalyst", as used herein, denotes the weight of the crystalline aluminosilicate which forms the base of the catalyst.

The isomerization reaction of this invention is carried out in the presence of hydrogen. The feed rate of hydrogen in this case can be varied widely according to the type of the aromatic hydrocarbon material and/or the catalyst, etc. Generally, it is appropriate to feed hydrogen at such a rate that the hydrogen/hydrocarbon mole ratio is generally from 0.1 to 15, preferably 1 to 10, more preferably from 1 to 8.

According to the isomerization reaction in accordance with the process of this invention, a xylene isomeric mixture which has not attained a thermodynamic equilibrium composition in the aromatic hydrocarbon feedstock is isomerized to a xylene isomeric mixture having a composition close to the thermodynamic equilibrium composition at the isomerization temperature. Simultaneously, ethylbenzene necessarily present in the isomeric mixture is selectively de-ethylated to benzene and ethane as main products.

When the palladium-containing zeolite catalyst is used in the isomerization of xylenes, a carbonaceous substance gradually deposits on the catalyst surface and its activity gradually decreases. Accordingly, when its activity is reduced to a predetermined activity level, the reaction is interrupted and the catalyst is reactivated.

Industrial plants are generally obligated to maintain and inspect isomerization reactors periodically. Moreover, in the event of a disorder or accident in the reactors or feed and/or product facilities these facilities must be opened for inspection or repair. When in such a case, the reaction is stopped and the reactor including a large amount of the active palladium-containing zeolite catalyst is opened to expose the catalyst to the air, a vigorous oxidation and exothermic reaction takes place to provoke a danger of explosion. In such a case, too, the mild oxidative burn-off step using an oxygen-containing gas in accordance with this invention can be very effectively applied to the catalyst. By this step, the reactivation of the catalyst and the removing of coke deposits on the catalyst can be performed simultaneously.

The interruption (stopping) of the isomerization reaction can be performed by first stopping the feeding of the aromatic hydrocarbon feedstock, then recovering the residual aromatic hydrocarbon as a drain while circulating hydrogen gas, replacing the hydrogen gas by an inert gas such as nitrogen gas, and adjusting the temperature of the catalyst bed to a regeneration initiating temperature.

After the isomerization reaction has been so stopped, the catalyst is subjected to regeneration treatment.

The regeneration treatment of the palladium-containing zeolite catalyst in accordance with this invention can be performed by introducing an oxygen-containing gas into the catalyst on the surface of which coke (a carbonaceous material) has been deposited to contact the catalyst with the oxygen-containing gas and oxidize palladium on the catalyst and simultaneously to burn off the coke deposits on the catalyst.

Burning off conditions are very important in order to provide a regenerated catalyst having activity close to its initial activity without decisively adverse effects on the ability of zeolite to catalyze isomerization of xylenes and the ability of palladium to catalyze selective deethylation of ethylbenzene. It is critical that the burning off should be carried out under the following conditions.

(a) Throughout the burning off period, the hot spot temperature of the catalyst bed is controlled not to exceed 50° C., preferably 30° C., more preferably 20° C.

(b) Introduction of the oxygen-containing gas is started when the temperature of the gas is relatively low, namely not higher than 200° C., preferably 50° to 190° C., more preferably about 100° to 180° C., thereby initiating the burn-off. Then, the burn-off is carried out while gradually increasing the temperature of the oxygen-containing gas to a temperature in the range of 330° to 390° C., preferably 350° to 380° C., more preferably about up to about 370° C.

(c) Care should be taken so that no part of the catalyst bed exceeds a maximum temperature of 400° C.

The "hot spot temperature" in the catalyst bed, as used herein, is determined as follows:

The surface temperature of the catalyst rises because of the heat generated by the burning of coke deposited on it. The temperature of the atmosphere near the surface of the catalyst is measured. The difference between the maximum temperature measured in the entire catalyst bed and the temperature of the regenerating gas at the inlet of the catalyst bed is defined as the hot spot temperature. The temperature of the gas at the inlet is nearly uniform in an adiabatic-type reactor, and the number of measuring sites may be small, and for example may be at least one. On the other hand, the temperature of the neighborhood of the catalyst surface varies greatly depending upon the site of the catalyst, and in order to know the maximum temperature at various points, a number of measuring sites properly arranged must be provided. The positions of the measuring sites vary depending upon the amount of the catalyst, the shape of the reactor containing the catalyst, the flow rate of the regenerating gas, etc. Such measuring sites should be provided in at least 3, preferably at least 5, levels, respectively, in the gas flowing direction of the catalyst bed and in a direction perpendicular to the gas flow.

The hot spot temperature can be controlled by properly adjusting the flow rate, temperature and total pressure of the oxygen-containing gas introduced into the catalyst bed, and/or the partial pressure of the oxygen in the gas.

The temperature of the oxygen-containing gas to be introduced into the catalyst bed can be continuously raised. Generally, stepwise raising is industrially advantageous. The stepwise raising of the temperature is performed preferably at intervals of 10° to 50° C., preferably 20° to 50° C. It is desirable that at each temperature level, the catalyst is allowed to stand until carbon oxide is no longer evolved from the catalyst bed, and thereafter, the temperature of the gas is raised to the next temperature level.

In a preferred embodiment of the present invention, the temperature of introducing the oxygen-containing gas into the catalyst bed can be raised stepwise from about 100° C. to about 390° C. at intervals of about 10° to 50° C.

During the first stage of the above temperature raising process in which the temperature is increased to about 200° C. (to be referred to as a first treating step), oxidation of palladium in the catalyst to palladium oxide takes place mainly, and in the latter stage of the temperature raising process (to be referred to as a second treating step), oxidation and burn-off of the coke deposited on the catalyst mainly occur.

In the first treating step, palladium metal present on the surface of the zeolite is oxidized substantially to palladium oxide. This oxidation occurs rapidly, and the heat of the oxidation reaction is high. Since this is likely to cause a local increase of the surface temperature of the catalyst, it is important that the first treating step should be carried out under mild conditions by minimizing the partial pressure of oxygen in the oxygen-containing gas to be introduced and very gradually increasing the temperature of the gas. Before introducing the oxygen-containing gas in the first treating step, combustible gases such as hydrocarbons and hydrogen in the oxygen-containing gas should be removed as much as possible by using an inert gas such as nitrogen.

As stated above, oxidation of palladium metal to palladium oxide takes place mainly in the first treating step. It is desirable that at this time, those substances in the coke deposited on the catalyst which can be burned at the temperature of the first treating step should be simultaneously burned at least partly. The time required for the first treating step is affected by the size of the catalyst bed, the temperature, etc., but should be the one which is sufficient to complete the oxidation of palladium metal to palladium oxide. Usually, a period of 1 minute to 20 hours is sufficient.

In the second treating step subsequent to the first treating step, burn-off of the coke deposited on the catalyst occurs mainly. In the second treating step, it is not necessary to completely burn off the burnable coke deposit on the catalyst surface. Even when a part of it remains unburned, the activity of the regenerated catalyst is high enough to achieve the objects of the present invention.

Preferably, in the second treating step, the temperature of the gas introduced is gradually raised while monitoring the state of the burning of the carbonaceous materials. When the temperature of the gas introduced is increased continuously, better results are obtained when the temperature is slowly increased so that at each temperature, the burnable coke deposits are fully burned. As a preferred embodiment of the present invention, when the temperature of the gas is raised non-continuously (stepwise), burn-off is carried out at a certain level of the gas temperature until coke deposits burnable at this temperature level are substantially removed, and thereafter, the gas temperature is raised to the next temperature level at which carbonaceous materials burnable at this level are substantially completely burned. This stepwise burning treatment is continued until the desired maximum temperature is reached.

The time required for the second treating step varies depending upon the amount of the coke deposits, their properties, the treating temperature and pressure, the flow rate of the treating gas, the concentration of oxygen in the treating gas, etc. In any case, it is desirable to analyze the gaseous burnt products periodically, and to continue the burn-off until evolution of carbon monoxide or carbon dioxide from the catalyst bed or consumption of oxygen substantially ceases. Usually, the suitable time is at least 1 hour, preferably at least several hours, especially preferably 5 to 200 hours.

The total treating time of the first and second treating steps is generally 5 to 500 hours, preferably 10 to 200 hours.

The oxygen-containing gas to be introduced into the catalyst bed in the burn-off step may consist only of pure oxygen, but generally, a mixture of oxygen with an inert gas such as nitrogen, argon or helium is suitable.

Desirably, the oxygen content of the treating gas is adjusted so that the partial pressure of oxygen at the time of introduction is generally in the range of 0.01 to 2.5 kg/cm$^2$.abs., preferably 0.02 to 1.5 kg/cm$^2$.abs. It is convenient that in the first stage of the burn-off step, the partial pressure of oxygen is relatively low, and in the latter stage, the partial pressure of oxygen is maintained relatively high. For example, it is preferred that in the first treating step, the partial pressure of oxygen is 0.01 to 2.0 kg/cm$^2$.abs., and in the second treating step, it is 0.01 to 2.5 kg/cm$^2$.abs.

In order to regenerate the catalyst advantageously, it is very important that the oxygen-containing gas should contain some water. It is very desirable that the water content of the gas at the time of introduction be adjusted generally to 500 to 50,000 ppm by volume, preferably 1,000 to 40,000 ppm by volume, and especially preferably 2,000 to 30,000 ppm by volume.

The water content of the treating gas can usually be controlled by controlling the pressure of the regenerating circulating gas and the temperature of the gas-liquid separator, and as required, adding water or steam to the gas.

If the water content of the oxygen-containing gas to be introduced is extremely low, the de-ethylating activity of the catalyst in the xylene isomerization reaction at the initial stage after regeneration is lower than when the water content of the regenerating gas is higher. On the other hand, when the water content of the gas is excessively high, there is noted a tendency that the acidic site on the zeolite catalyst is damaged and its ability to catalyze isomerization of xylenes decreases.

Another important requirement in the burn-off step is that the introduction of the heated oxygen-containing gas should be controlled so that no part of the catalyst bed exceeds a maximum temperature of 400° C. This control can be achieved by controlling the temperature and flow rate of the gas to be introduced into the catalyst bed, and/or the oxygen content of the gas, or controlling the rate of temperature raising. If the maximum temperature of the catalyst bed exceeds 400° C., the resulting catalyst does not exhibit the original high activity in the isomerization of xylene, and particularly, has a reduced de-ethylating activity. This is presumably because treatment at a temperature higher than 400° C. causes agglomeration of dispersed palladium oxide, and when the palladium oxide is reduced, deposition of coke on the surface of the agglomerated metallic palladium is accelerated and consequently, the de-ethylating activity of the catalyst considered to be dependent on palladium metal is reduced.

The catalyst subjected to the burn-off step in the above-described manner contains palladium on zeolite as an oxide. Accordingly, the catalyst is purged with an inert gas such as nitrogen after the burn-off step so as to avoid inclusion of oxygen. Then, it is heat-treated at a temperature of at least 200° C., preferably 300° to 500° C., under atmospheric or elevated pressure using a hydrogen-containing gas to reduce palladium in the oxidized state to metallic palladium. The amount of hydrogen required in this reduction is preferably at least 10 molar times the theoretical amount required to convert palladium oxide to metallic palladium. The time required for this hydrogen reduction depends upon the reducing temperature, the amount of the catalyst (the amount of palladium), the reducing pressure, the concentration of hydrogen, the flow rate of the hydrogen-containing gas, etc. Usually, it is at least 30 minutes, preferably at least 1 hour, especially preferably 1 to 10 hours.

U.S. Pat. No. 3,986,982 cited hereinabove teaches that the catalyst subjected to the burn-off treatment is then treated with chlorine before purging with the inert gas. According to the present invention, the regenerated catalyst attains the original high activity without such chlorine treatment, and therefore, the chlorine treatment is not required in the process of the present invention.

The isomerization reaction of xylenes can be continued by again feeding the aromatic hydrocarbon feedstock to the catalyst so subjected to reducing and reactivating operations.

The process of xylene isomerization in accordance with this invention brings about the following technical advantages.

By using a zeolite containing palladium as a catalyst in accordance with this invention, a high p-xylene approach to equilibrium, a high ethylbenzene decomposition ratio and a high de-ethylation ratio can be attained under mild conditions involving a relatively low temperature and a high WHSV. Moreover, hydrogenation of the benzene ring is very much reduced, a xylene loss ascribable to the formation of naphthenes and a xylene loss owing to de-methylation are little. Furthermore, since the catalyst can be used under mild conditions, its activity is not appreciably reduced even when used for a long period of time.

The activity of the catalyst regenerated by the process of this invention is equal to the initial high activity of the catalyst. It is one objective of this invention to perform isomerization of xylenes with a high de-ethylation activity. A palladium-containing zeolite catalyst undergoes a reduction in de-ethylating activity after conventional regeneration. In contrast, the reduction of the de-ethylating activity can be completely prevented by the regenerating method in accordance with this invention, and the original high activity level can be retained. This is a great feature of the process of this invention.

The following Examples illustrate the present invention more specifically with the aid of the accompanying drawings in which:

FIG. 1 includes graphic representations of various reaction indicates plotted as a function of reaction time, based on the data in Example 2; and, FIG. 2 indicates graphic representations of various reaction indices plotted as a function of time, based on the data in Comparative Example 1.

EXAMPLE 1 (CATALYST PREPARATION)

(a) Preparation of H/ZSM-5

A zeolite was synthesized in accordance with the method disclosed in U.S. Pat. No. 3,965,207. In the synthesis, n-propylamine and n-propyl bromide were added as organic cation sources. The synthesized product was identified as ZSM-5 by its X-ray diffraction pattern. The resulting synthetic product was filtered, fully washed with water, and dried in an electric dryer at 100° C. for 8 hours and at 200° C. for 16 hours, and then calcined at 500° C. for 16 hours in a current of air in an electrical muffle furnace. Then, 250 g of the synthetic product was subjected to ion exchanging in 1.5 liters of a 5% by weight aqueous solution of ammonium chloride at 80° C. for 24 hours. This operation was repeated two times further, and then, the product was fully washed with water, dried in an electrical dryer at 100° C. for 8 hours and then at 200° C. for 16 hours, and further calcined in an electrical muffle furnace at 450° C. for 16 hours in a current of air to obtain H-form ZSM-5 (abbreviated as H/ZSM-5). This zeolite had a sodium content of 0.05% by weight and a silica/alumina mole ratio of 92.

(b) Preparation of Pd/ZSM-5

0.186 g of $[Pd(NH_3)_4]Cl_2 \cdot H_2O$ was dissolved in 2.5% aqueous ammonia, and 15 g of H/ZSM-5 obtained by the method of (a) above was added to the solution. With occasional shaking, the zeolite was dipped in the solution for 8 hours at 70° C., filtered and washed fully at room temperature. Then, it was dried in an electrical dryer at 100° C. for 4 hours and then at 200° C. for 4 hours, and calcined in an electrical muffle furnace at 450° C. for 4 hours in a current of air to obtain Pd/ZSM-5. This product contained 0.44%, based on its total weight, of palladium. This product is referred to hereinbelow as a catalyst A.

Catalysts B, C, D and E containing 0.45 to 0.47% by weight of palladium were separately prepared by the same method as above.

A catalyst F was prepared as follows:

Pure water (50 ml) was added to 0.050 g of commercial palladium chloride powder, and 3.0 ml of 1 N hydrochloric acid solution was further added to dissolve the palladium chloride completely. The pH of the solution at this time was about 1. To the solution was added 6.0 g of H/ZSM-5 obtained by the method (a), and with occasional shaking, it was dipped for 2 hours at 70° C. Then, it was evaporated to dryness at less than 50° C. under reduced pressure using a rotary evaporator. The residue was dried in an electrical dryer at 100° C. for 4 hours and 200° C. for 4 hours, and then calcined in an electrical muffle furnace at 450° C. for 4 hours in a current of air. The product contained 0.46%, based on its total weight, of palladium.

EXAMPLE 2

The powdery catalyst A obtained in Example 1 and alumina gel for chromatography (below 300 mesh) were fully mixed in a weight ratio of 1:1, and molded into a size of 10 to 20 mesh. The molded article was calcined in an electrical muffle furnace at 450° C. for 4 hours in an atmosphere of air, and then filled in a reactor of the fixed bed flowing type. Then, it was subjected to reducing treatment in a stream of hydrogen at 350° C. under atmospheric pressure, and a subsequently, a xylene isomeric mixture of the composition shown in Table 1 was isomerized in the reactor (first cycle). The reaction conditions were as follows:

Reaction temperature: 350° C.
WHSV: 8.0 hr$^{-1}$ (based on the zeolite)
Hydrogen/aromatic hydrocarbon mole ratio: 3/1
Pressure: 120 psia After the first cycle of the reaction, burnable substances in the system were fully purged with nitrogen gas, and the temperature of the catalyst bed was lowered to 200° C. Air containing about 5,000 ppm by volume of steam was passed through the catalyst bed under atmospheric pressure for 4 hours to burn off carbonaceous substances deposited during the reaction. The flow rate of the regenerating air was about 300 volumes/volume/hour.

After the first regeneration, the regenerating air was purged by using nitrogen, and then the temperature of the catalyst bed was raised to 350° C. The carrier gas was changed to hydrogen, and the catalyst was reduced with hydrogen. Then, under the same reaction conditions as above, the second cycle of the isomerization reaction was performed.

After the second cycle, burnable gases were purged by using nitrogen gas, the catalyst was regenerated with air containing about 5,000 ppm by volume of steam under atmospheric pressure at 200° C. for 3 hours, at 250° C. for 1.5 hours, at 300° C. for 1.5 hours and at 350° C. for 2 hours. After the second regeneration, the regenerating air was purged with nitrogen gas, and the third cycle of the isomerization reaction was performed under the aforesaid reaction conditions.

After the third cycle, burnable gases were purged with nitrogen gas, and the atalyst was regenerated with air containing about 5,000 ppm by volume of steam at atmospheric pressure at 200° C. for 3 hours, at 350° C. for 4 hours, at 400° C. for 2 hours, and then at 450° C. for 2 hours. After the third regeneration, the regenerating air was purged with nitrogen gas, and the fourth cycle of the isomerization was performed under the reaction conditions.

[The rise of the temperature of the catalyst bed owing to the burning of coke deposits (hot spot) was below 10° C. in all cases.]

The composition of the product in each cycle at a time when the activity of the catalyst was stable and the reaction indices in each cycle are shown in Table 1. Changes with time of the reaction indices are plotted in FIG. 1.

It is noted from the results obtained that when the regeneration of the catalyst is carried out only at 200° C. the reduction of the catalytic activity, especially the de-ethylating activity, of the catalyst owing to the regeneration is very little, but a reduction in the ethylbenzene decomposing activity is noted. When the initial regeneration temperature is set at 200° C., and finally the regenerating temperature is raised finally to 350° C., both the de-ethylating activity and the ethylbenzene decomposing activity are reduced only very slightly. On the other hand, it is clear that when the initial regenerating temperature is set at 200° C. but the regenerating temperature is raised to 450° C. at a maximum, the activity, especially the de-ethylating activity, of the catalyst is markedly reduced.

After the fourth cycle, the catalyst was regenerated at each of the various regenerating temperatures shown in Table 2. The results are shown in Table 2. From the results obtained, it is seen that carbonaceous materials are burned already at a temperature of as low as 150° C.

TABLE 1

| CATALYST REGENERATING OPERATION | | | | |
|---|---|---|---|---|
| Number of catalyst regenerating cycles | Fresh | 1 | 2 | 2 |

TABLE 1-continued

|  | 200 × 4 | 200 × 3<br>250 × 1.5<br>300 × 1.5<br>350 × 2 | 200 × 3<br>350 × 4<br>400 × 2<br>450 × 2 |
|---|---|---|---|
| Regenerating temperature (°C.) × time (hours) | | | |

XYLENE ISOMERIZING ACTIVITY AFTER CATALYST REGENERATION

| Number of cycles | 1 | 2 | 3 | 4 |
|---|---|---|---|---|
| Time on stream (hours) | 104 | 90 | 123 | 112 |
| $C_2$-$C_4$ paraffin | 1.98 | 1.91 | 1.96 | 1.57 |
| $C_5$-$C_9$ NA* | 0.22 | 0.16 | 0.14 | 0.14 |
| benzene (BZ) | 6.27 | 6.04 | 6.20 | 5.51 |
| toluene (Tol) | 2.73 | 2.58 | 2.71 | 3.18 |
| ethylbenzene (EB) | 5.53 | 5.88 | 5.67 | 6.17 |
| p-xylene (PX) | 19.57 | 19.59 | 19.52 | 19.21 |
| m-xylene (MX) | 43.74 | 43.75 | 43.54 | 42.87 |
| o-xylene (OX) | 18.06 | 18.14 | 18.05 | 17.84 |
| $C_9$ aromatics ($C_9$Ar) | 1.03 | 0.97 | 1.02 | 1.41 |
| $C_{10}^+$ aromatics ($C_{10}^+$Ar) | 0.87 | 0.98 | 1.19 | 2.10 |
| PX approach to equilibrium (%) | 102.8 | 102.6 | 102.7 | 102.6 |
| EB decomposition ratio (%) | 63.0 | 60.7 | 61.8 | 58.5 |
| Xylene loss (%) | 2.63 | 2.51 | 3.00 | 4.41 |
| De-ethylation ratio (%) | 87.0 | 85.4 | 83.7 | 69.2 |

Composition of the feedstock

| Cycles | $C_5$-$C_9$N | Tol | EB | PX | MX | OX | $C_9$Ar |  |
|---|---|---|---|---|---|---|---|---|
| 1, 2 | 0.04 | 1.41 | 14.95 | 9.31 | 56.13 | 18.13 | 0.03 | wt % |
| 3, 4 | 0.04 | 1.41 | 14.85 | 9.12 | 56.60 | 17.89 | 0.09 | wt % |

*NA in the table denotes non-aromatic hydrocarbons (predominantly of paraffins and naphthenes).

The various reaction indices are defined as follows:

$$\text{PX approach to equilibrium (\%)} = \frac{[PX]_P - [PX]_F}{[PX]_E - [PX]_F} \times 100$$

$$\text{EB decomposition ratio (\%)} = \frac{[EB]_F - [EB]_P}{[EB]_F} \times 100$$

$$\text{Xylene loss (\%)} = \frac{[X]_F - [X]_P}{[X]_F} \times 100$$

$$\text{De-ethylation ratio (\%)} = \frac{\text{Total moles of EB lost} - \text{Moles of EB lost in disproportionation and transalkylation}}{\text{Total moles of EB lost}} \times 100$$

The abbreviations mean the following.

- $[PX]_F$: the concentration (wt.%) of p-xylene in the three isomers of xylene in the feedstock
- $[PX]_P$: the concentration (wt.%) of p-xylene in the three isomers of xylene in the product
- $[PX]_E$: the equilibrium concentration (wt.%) of p-xylene in the xylene isomers at the reaction temperature
- $[EB]_F$: the concentration (wt.%) of ethylbenzene in the feedstock
- $[EB]_P$: the concentration (wt.%) of ethylbenzene in the product
- $[X]_F$: the concentration (wt.%) of the three xylene isomers in the feedstock
- $[X]_P$: the concentration (wt.%) of the three xylene isomers in the product

TABLE 2

Catalyst A (used in the fourth cycle)

| Regenerating temperature (°C.) | Regenerating time (hours) | Amount of burned carbon (wt.%) | Ratio (%) |
|---|---|---|---|
| 100 | 2 | 0.03 | 1.4 |
| 150 | 2 | 0.42 | 19.3 |
| 200 | 2 | 0.32 | 14.7 |
| 250 | 2 | } 1.41 | } 64.6 |
| 300 | 2 | | |
| 350 | 1 | | |
| 400 | 1 | | |
| 450 | 2 | | |
| Total |  | 2.18 | 100.00 |

Note:
The amount of burned carbon is based on the weight of zeolite.

EXAMPLE 3

The catalyst B obtained in Example 1 was treated in the same way as in Example 2, and in the presence of the treated catalyst B, xylenes were isomerized under the same reaction conditions as in Example 2. The reaction indices and the temperature and time of catalyst regeneration with air at atmospheric pressure, and the amount of carbon burned at the time when the activity of the catalyst was stable in each cycle are shown in Table 3. In these regenerating operations, the regenerating air contained about 5,000 ppm by volume of steam. The hot spot temperature was below 10° C. in all cases.

When the initial regenerating temperature was lowered to 150° C. and the maximum regenerating temperature was adjusted to 350° C. as in the regeneration after the first cycle, no reduction in activity was noted. However, when the initial regenerating temperature was raised to 220° C. as in the regeneration after the second cycle, the de-ethylating activity showed some decrease. It is evident therefore that better results can be obtained by adjusting the initial regenerating temperature to not more than 200° C. It is also seen that when the initial regenerating temperature is 150° C. as in the regenerating operation after the third cycle but the maximum regenerating temperature is raised to 400° C., the de-ethylation ratio is considerably reduced. It is apparent from this that the maximum regenerating temperature is preferably adjusted to below 400° C.

TABLE 3

CATALYST REGENERATING OPERATION

| Number of catalyst regenerating cycles | Fresh | 1 | 2 | 3 |
|---|---|---|---|---|
| Regenerating temperature (°C.) × time (hours) (amount of carbon burned based on zeolite) |  | 150 × 25 (0.13)<br>200 × 2 (0.29)<br>250 × 2 (0.35)<br>300 × 2 (0.30)<br>350 × 2 (0.32) | 220 × 3 (0.32)<br>260 × 2 (0.25)<br>300 × 2 (0.34)<br>350 × 2 (0.21) | 150 × 3 (0.22)<br>200 × 2 (0.34)<br>250 × 2 (0.29)<br>300 × 2 (0.31)<br>350 × 2 (0.23)<br>400 × 2 (0.27) |

XYLENE ISOMERIZING ACTIVITY AFTER CATALYST REGENERATION

| Number of cycles | 1 | 2 | 3 | 4 |
|---|---|---|---|---|
| Time on stream (hours) | 124 | 128 | 127 | 124 |
| PX approach to equilibrium (%) | 103.0 | 103.0 | 103.0 | 103.0 |
| EB decomposition ratio (%) | 50.2 | 50.1 | 52.3 | 49.2 |
| Xylene loss (%) | 1.76 | 1.70 | 2.17 | 2.45 |
| De-ethylation ratio (%) | 80.3 | 80.4 | 77.9 | 71.6 |

EXAMPLE 4

A model experiment was conducted in order to ascertain the oxidizability of palladium in the first treating step. Commercial palladium chloride was fully pulverized, and then reduced to metallic palladium [Pd°] in a hydrogen stream at 350° C. under atmospheric pressure. Then, the metallic palladium was oxidized under various conditions in a stream of air under atmospheric pressure, and the amount of palladium in the product was determined. The results obtained are shown in Table 4.

The results demonstrate that at 50° C., palladium could be oxidized, but it requires a long period of time. When it is desired to oxidize metallic palladium completely, a period of 15 hours is required at 100° C., but at 150° C., a period of 2 hours is sufficient. It is presumed that since the amount of palladium supported on the catalyst actually used is small and palladium has good dispersibility, it will be more rapidly oxidized under these conditions.

TABLE 4

| Method of treatment | Temperature (°C.) | Time (hours) | Pd (found; wt. %) | Pd (calculated; wt. %) |
|---|---|---|---|---|
| Hydrogen reduction of PdCl$_2$ | 350 | 1 | 99.2 | 100.0* |
| Air oxidation of Pd° (1) | 50 | 18 | 91.3 | 86.9** |
| Air oxidation of Pd° (2) | 100 | 4 | 90.3 | " |
| Air oxidation of Pd° (3) | 100 | 15 | 86.8 | " |
| Air oxidation of Pd° (4) | 150 | 2 | 86.9 | " |
| Air oxidation of Pd° (5) | 200 | 1 | 86.7 | " |

*Pd°,
**PdO

EXAMPLE 5

In order to further illustrate the significance of the lower limit (200° C.) of the initial regenerating temperature, the following model experiment was performed. Specifically, the repetition of regeneration in a commercial catalyst was taken into consideration, and the catalyst C was repeatedly reduced with hydrogen and oxidized with air at at 150° C. and 220° C. respectively, and then using the regenerated catalyst C, xylenes were isomerized at atmospheric pressure using a fixed bed flowing type reactor. In this case, the oxidizing air contained about 5,000 ppm by volume of steam. The reaction conditions were as follows:
Reaction temperature: 350° C.
WHSV: 9.1 hr$^{-1}$ (based on zeolite)
Hydrogen/aromatic hydrocarbon mole ratio: 1/1
Pressure: atmospheric pressure
Composition of the feedstock: the same as in Example 2

The characteristics of the reaction 18 hours after starting to pass the feedstock are shown in Table 5.

It is seen from the results obtained that when the cycle of reduction with hydrogen and oxidation with air was repeated, the reduction in catalytic activity was lower at 150° C. than at 220° C. Accordingly, when the regeneration is to be repeated, the initial regenerating temperature should better be below 200° C.

TABLE 5

|  | 1 | 2 |
|---|---|---|
| Temperature of the regenerating air (°C.) | 150 | 200 |
| Time (hours) | 2 | 2 |
| Cycles | 8 | 8 |
| Hydrogen reduction temperature (°C.) | 150 | 220 |
| Time (hours) | 2 | 2 |
| Cycles | 8 | 8 |
| PX approach to equilibrium (%) | 92.1 | 76.1 |
| EB decomposition ratio (%) | 22.1 | 18.6 |
| Xylene loss (%) | 0.34 | 0.26 |
| De-ethylation ratio (%) | 78.0 | 76.8 |

EXAMPLE 6

Catalyst regeneration was performed using an oxygen-containing gas having a lower partial pressure of oxygen than in Examples 2 to 5.

The catalyst F obtained in Example 1 was treated in the same way as in Example 2, and using the treated catalyst F, xylenes were isomerized under the same reaction conditions as in Example 2. The reaction indices at the time when the activity of the catalyst was stable, and the oxygen concentration (partial pressure of oxygen) of the regenerating gas, the temperature and time, and the amount of carbon burned during regeneration at atmospheric pressure are shown in Table 6. In these regenerating procedures, the regenerating gases all contained about 5,000 ppm by volume of steam with the balance being nitrogen. The hot spot temperature was below 10° C. in all cases.

TABLE 6

| CATALYST REGENERATING OPERATION | | | |
|---|---|---|---|
| Number of catalyst regenerating cycles | Fresh | 1 | 2 |
| Regenerating temperature (°C.) × time (hours) × oxygen concentration (vol.%) [oxygen partial pressure (kg/cm$^2$)] | [0.05] 300 × 4 × 5 | 150 × 2 × 1 [0.01] 150 × 2 × 5 [0.05] 200 × 2 × 5 [0.05] 250 × 2 × 5 [0.05] 300 × 2 × 5 [0.05] 350 × 4 × 10 [0.10] 350 × 2 × 21 [0.21] | 350 × 3.5 × 1 [0.01] 350 × 3 × 5 [0.05] 350 × 3 × 10 [0.10] 350 × 2 × 21 [0.21] |
| Amount of carbon burned (wt.%) |  | 1.07 | 1.03 |
| XYLENE ISOMERIZING ACTIVITY AFTER CATALYST REGENERATION | | | |
| Number of cycles | 1 | 2 | 3 |
| Time on steam (hours) (hours) | 131 | 136 | 140 |
| PX approach to equilibrium (%) | 102.9 | 102.9 | 102.8 |
| EB decomposition ratio (%) | 49.9 | 49.4 | 50.4 |
| Xylene loss (%) | 2.35 | 1.85 | 2.08 |
| De-ethylation ratio (%) | 81.7 | 80.6 | 77.3 |

When as in the regeneration after the first cycle, the initial regenerating temperature was lowered to 150° C., the maximum regenerating temperature was adjusted to 350° C., and the concentration of oxygen (partial pressure of oxygen) was decreased to below 21% by volume (0.21 kg/cm$^2$) in Examples 2 to 5, the activity of the catalyst fully returned to the original level, and there was scarcely noted any decrease in de-ethylating activity. On the other hand, when as in the regeneration after the second cycle, the oxygen concentration (partial pressure of oxygen) was low but the regenerating temperature was as high as 350° C., the activity of the catalyst returned to the original level but the de-ethylating activity decreased. Thus, the initial regenerating temperature exerts a great influence.

EXAMPLE 7

In this Example, the effect of the water content of the regenerating gas was examined.

The catalyst used in the third cycle in Example 6 was taken out of the reactor after its temperature was lowered while passing nitrogen through the catalyst bed. It was divided into three equal portions, and each of them was regenerated under atmospheric pressure using a regenerating gas having a varying water content.

The regeneration was carried out in a horizontal type electrical circular furnace using air (partial pressure of oxygen: 0.21 kg/cm$^2$) having a water content of less than 50, about 5,000, and about 25,000 ppm by volume respectively with other conditions being maintained constant. The regenerating temperature was 350° C., and the regenerating time was 6 hours.

Using each of the regenerated catalysts, a xylene isomeric mixture was isomerized in a reactor of the fixed bed flowing type under atmospheric pressure. The reaction conditions were as follows:

Reaction temperature: 350° C.
WHSV: 8.0 hour$^{-1}$ (based on zeolite)
Hydrogen/aromatic hydrocarbon mole ratio: 1/1
Pressure: atmospheric pressure
Composition of the feedstock: the same as in Example 2

Changes in the de-ethylation ratio with varying the time on stream were determined at each water content level, and the results are shown in Table 7.

From the results obtained, it is seen that when the water content of the regenerating gas is low, the reduction of the de-ethylation ratio for a certain period after the initiation of the reaction is remarkable. Accordingly, in order to cause the regenerated catalyst to exhibit the same performance as the fresh catalyst from the outset of the reaction, it is necessary to maintain a high water content of the regenerating gas.

TABLE 7

| Water content (ppm by volume) | <50 | 5,000 | 25,000 |
|---|---|---|---|
| | Time on stream (hours) | | |
| Deethylation ratio (%) | 2 | 61.2 | 64.0 | 67.2 |
| | 12 | 53.8 | 56.6 | 62.6 |
| | 24 | 49.1 | 49.2 | 57.8 |
| | 48 | 46.3 | 46.5 | 53.5 |
| | 72 | 44.3 | 44.6 | 46.8 |
| | 96 | 44.2 | 44.3 | 44.5 |
| | 120 | 44.1 | 44.0 | 44.3 |

COMPARATIVE EXAMPLE 1

The catalyst D obtained in Example 1 was treated in the same way as in Example 2, and using the treated catalyst D, a xylene isomeric mixture was isomerized under the same reaction conditions as in Example 2. The reaction indices at the time when the activity of the catalyst was stable in each cycle are shown in Table 8.

Changes with time of the reaction indices are shown in FIG. 2. After the first cycle, the catalyst was regenerated at 350° C. under atmospheric pressure for 5 hours, and then at 350° C. under a pressure of 4 kg/cm$^2$.G for 1 hour. After the second cycle, the catalyst was regenerated at 350° C. under atmospheric pressure for 6 hours and then at 350° C. under a pressure of 4 kg/cm$^2$.G for 16 hours.

It is seen from the results obtained that when the initial regenerating temperature was set at 350° C., the activity, especially the de-ethylation ratio, of the catalyst at the time when it was stable decreased drastically as a result of the regeneration.

COMPARATIVE EXAMPLE 2

The catalyst E obtained in Example 1 was treated in the samed way as in Example 2, and in the presence of the treated catalyst E, a xylene isomeric mixture was isomerized under the same reaction conditions as in Example 2. After the first cycle, the catalyst was regenerated with air at 350° C. under atmospheric pressure for 2 hours. The reaction indices at the time when the activity of the catalyst was stable in each cycle are shown in Table 9.

It is seen that even when the regenerating time is shortened to 2 hours, the reduction of the de-ethylation ratio was great, and the initial regenerating temperature exerted a greater influence on the reduction of the de-ethylating activity than does the regenerating time.

TABLE 8

| Number of cycles | 1 | 2 | 3 |
|---|---|---|---|
| Time on stream (hours) | 108 | 99 | 122 |
| PX approach to equilibrium (%) | 102.7 | 102.7 | 102.5 |
| EB decomposition ratio (%) | 56.0 | 53.8 | 53.8 |
| Xylene loss (%) | 1.63 | 2.59 | 3.35 |
| De-ethylation ratio (%) | 91.4 | 81.6 | 71.5 |

TABLE 9

| Number of cycles | 1 | 2 |
|---|---|---|
| Time on stream (hours) | 121 | 95 |
| PX approach to equilibrium (%) | 102.8 | 102.9 |
| EB decomposition ratio (%) | 47.9 | 46.4 |
| Xylene loss (%) | 2.16 | 2.24 |
| De-ethylation ratio (%) | 80.4 | 74.2 |

What we claim is:

1. A process for isomerizing xylenes, which comprises
   contacting an aromatic hydrocarbon feedstock containing mainly a xylene isomeric mixture containing ethylbenzene with a catalyst of a palladium-containing crystalline aluminosilicate in the vapor phase in the presence of hydrogen to continuously isomerize xylenes and simultaneously de-ethylate the ethylbenzene selectively;
   interrupting the isomerization reaction;
   introducing an oxygen-containing gas into a bed of the catalyst in which coke has been deposited during the isomerization reaction, to contact the catalyst with the oxygen-containing gas;
   burning off the coke deposits on the catalyst with the oxygen-containing gas by gradually increasing the temperature of introduction of the oxygen-containing gas from not more than 200° C. to a temperature in the range of 330° to 390° C. with no part of the catalyst bed exceeding a maximum temperature of 400° C. while controlling the hot spot temperature of the catalyst bed not to exceed 50° C. throughout the burn-off period;

reducing in hydrogen the catalyst from which the burnable coke deposits have been removed at least partly;

and thereafter resuming the isomerization reaction in the presence of the regenerated catalyst.

2. The process of claim 1 wherein the oxygen-containing gas to be introduced into the catalyst bed contains 500 to 50,000 ppm by volume of water.

3. The process of claim 1 wherein the catalyst contains 0.01 to 2% by weight of palladium based on the weight of the crystalline aluminosilicate.

4. The process of claim 1 wherein the aluminosilicate has a silica/alumina mole ratio of from 20 to 1,000.

5. The process of claim 4 wherein the aluminosilicate is selected from the group consisting of zeolite ZSM-5, zeolite ZSM-11, zeolite ZSM-12, zeolite ZSM-35 and zeolite ZSM-38.

6. The process of claim 1 wherein the aluminosilicate is zeolite ZSM-5.

7. The process of claim 1 wherein the burn-off is carried out so that the hot spot temperature of the catalyst bed does not exceed 30° C.

8. The process of claim 1 wherein the temperature of the oxygen-containing gas introduced into the catalyst bed is increased gradually from about 150° C. to about 370° C.

9. The process of claim 1 wherein the gradual increase of the temperature of the oxygen-containing gas is performed stepwise.

10. The process of claim 9 wherein the stepwise temperature increase is performed at intervals of 10° to 50° C.

11. The process of claim 9 wherein the burn-off is carried out at each temperature level until carbon oxides no longer evolve.

12. The process of claim 1 wherein the temperature increasing is carried out over the course of about 5 to about 500 hours.

13. The process of claim 1 wherein the oxygen-containing gas is introduced at a partial oxygen pressure of 0.01 to 2.5 kg/cm$^2$/abs.

14. The process of claim 1 wherein the reaction is carried out at a temperature of 250° to 450° C.

15. The process of claim 1 wherein the reaction is carried out at a hydrogen partial pressure of 0 to 25 kg/cm$^2$.G.

16. The process of claim 1 wherein the aromatic hydrocarbon feedstock contains at least 30% by weight of the xylene isomeric mixture.

17. The process of claim 1 wherein the aromatic hydrocarbon feedstock contains at most 40% by weight of ethylbenzene.

18. The process of claim 1 wherein at least 80% by weight of the aromatic hydrocarbon feedstock consists of the xylene isomers and ethylbenzene.

19. The process of claim 1 wherein the aromatic hydrocarbon feedstock is fed at a weight hourly spaced velocity of about 1 to about 500 hr$^{-1}$.

20. The process of claim 1 wherein hydrogen is fed at such a rate that the mole ratio of hydrogen to the aromatic hydrocarbon feedstock is from 0.1:1 to 15:1.

* * * * *

UNITED STATES PATENT AND TRADEMARK OFFICE
CERTIFICATE OF CORRECTION

PATENT NO. : 4,300,014
DATED : November 10, 1981
INVENTOR(S) : Yasuo Yamasaki et al It is certified that error appears in the above—identified patent and that said Letters Patent is hereby corrected as shown below:

On the title page, item (75) fourth inventor should read:
-- Koji Sumitani --.

Signed and Sealed this

Sixth Day of July 1982

[SEAL]

Attest:

GERALD J. MOSSINGHOFF

Attesting Officer

Commissioner of Patents and Trademarks